United States Patent
Hatano et al.

(10) Patent No.: US 11,464,399 B2
(45) Date of Patent: Oct. 11, 2022

(54) BENDING OPERATION MECHANISM OF ENDOSCOPE

(71) Applicant: Olympus Corporation, Hachioji (JP)

(72) Inventors: Keisuke Hatano, Koganei (JP); Yutaro Watanabe, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 524 days.

(21) Appl. No.: 16/240,235

(22) Filed: Jan. 4, 2019

(65) Prior Publication Data
US 2019/0133419 A1 May 9, 2019

Related U.S. Application Data

(63) Continuation of application No. PCT/JP2017/016175, filed on Apr. 24, 2017.

(30) Foreign Application Priority Data

Jul. 12, 2016 (JP) .............................. JP2016-137873

(51) Int. Cl.
*A61B 1/005* (2006.01)
*A61B 34/00* (2016.01)
*A61B 1/00* (2006.01)

(52) U.S. Cl.
CPC .......... *A61B 1/0055* (2013.01); *A61B 1/0052* (2013.01); *A61B 1/0057* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 4,893,613 A * 1/1990 Hake ................... A61B 1/0053
600/152
5,159,446 A * 10/1992 Hibino ............... A61B 1/00039
600/152
(Continued)

FOREIGN PATENT DOCUMENTS

JP     2003-135385     5/2003
JP     2004-321612    11/2004
(Continued)

OTHER PUBLICATIONS

International Search Report and Written Opinion from corresponding International Application No. PCT/JP2017/016175, dated Jul. 4, 2017.

*Primary Examiner* — Ryan N Henderson
(74) *Attorney, Agent, or Firm* — Oliff PLC (57) ABSTRACT

A bending operation mechanism of an endoscope includes a bending operation lever, a seal unit having a tubular member and an elastic member. The elastic member has a fixed part attached to an outer circumference of the tubular member in a circumferential manner along a longitudinal axis direction N of the tubular member. An extending part that extends from an outer circumference of the fixed part to the outside of the fixed part in a radial direction K into a shape of a circle substantially concentric with the fixed part. A region extends from the outer circumference of the fixed part would extend with a predetermined angle.

13 Claims, 4 Drawing Sheets

(52) U.S. Cl.
CPC .......... *A61B 1/00066* (2013.01); *A61B 34/74* (2016.02); *A61B 2034/742* (2016.02)

(58) Field of Classification Search
CPC ... A61B 1/0056; A61B 1/0057; A61B 1/0058; A61B 1/008; A61B 1/00066; A61B 1/00068; A61B 2017/003; A61B 2017/00318; A61B 2017/00323; A61B 2017/00327; A61B 34/74; A61B 2034/742; A61M 25/0133; A61M 25/0136; A61M 25/0147

See application file for complete search history.

(56) References Cited

U.S. PATENT DOCUMENTS

| | | | | |
|---|---|---|---|---|
| 8,578,808 | B2* | 11/2013 | Koitabashi | ............... G05G 5/04 74/471 XY |
| 9,500,851 | B2* | 11/2016 | Yasunaga | ............. A61B 1/0057 |
| 9,743,827 | B2* | 8/2017 | Yasunaga | ............. A61B 1/0057 |
| 2004/0193014 | A1* | 9/2004 | Miyagi | ................ A61B 1/0052 600/118 |
| 2004/0267093 | A1* | 12/2004 | Miyagi | ................ A61B 1/0016 600/152 |
| 2007/0265500 | A1 | 11/2007 | Koitabashi et al. | |
| 2008/0275303 | A1* | 11/2008 | Koitabashi | .......... A61B 1/00042 600/146 |
| 2009/0149709 | A1* | 6/2009 | Koitabashi | .......... A61B 1/00149 600/131 |
| 2012/0209068 | A1* | 8/2012 | Hosaka | .............. G02B 23/2476 600/109 |
| 2014/0148646 | A1* | 5/2014 | Inada | .................... A61B 1/0057 600/149 |

FOREIGN PATENT DOCUMENTS

| | | | | |
|---|---|---|---|---|
| JP | 2005-279119 | | 10/2005 | |
| JP | 2006-192201 | | 7/2006 | |
| JP | 2008036355 | A * | 2/2008 | ......... A61B 1/00149 |
| JP | 2013052078 | A * | 3/2013 | |
| JP | 2013-088505 | | 5/2013 | |
| JP | 2016-052422 | | 4/2016 | |
| WO | 2008018554 | | 2/2008 | |

* cited by examiner

BENDING OPERATION MECHANISM OF ENDOSCOPE

CROSS-REFERENCE TO RELATED APPLICATIONS

This application is a continuation application of PCT Application No. PCT/JP2017/016175 filed on Apr. 24, 2017, which in turn claim priority to the Japanese Patent Application No. 2016-137873 filed on Jul. 12, 2016 in Japan which is hereby incorporated by reference in its entirety.

TECHNICAL FIELD

The technology disclosed herein relates to a bending operation mechanism of an endoscope. The endoscope includes a seal unit externally mounted on a shaft body of a bending operation lever. The bending operation lever is tilted to bend a bending part provided at an insertion unit of the endoscope.

DESCRIPTION OF THE RELATED ART

In recent years, various endoscopes have been widely used in the medical field. With the endoscope used in the medical field, a suspected site in a body cavity can be observed by inserting a thin, long insertion unit into the body cavity of a subject. Furthermore, a configuration is well known in which for example, a bending part is provided on the distal end of the insertion unit of an endoscope. In this configuration, the bending part can freely bend in multiple directions.

The bending part improves insertability of the insertion unit at a flexural part in the body cavity. In addition, the bending part allows change in the observation direction of an observation optical system in the insertion unit. The observation optical system is located at a distal part. The distal part is located on the distal end relative to the bending part. For example, an endoscope includes an insertion unit and an operation unit that is located consecutively in the proximal end of the insertion unit. In the insertion unit and in the operation unit, one pair or two pairs of wires, i.e. two or four wires, are inserted. Each wire has a distal end attached to the bending part.

The operation unit includes a bending operation member, for example, a bending operation lever in a known joystick device. Any of the four wires is pulled in association with tilt operation of the bending operation member. Due to this, the bending part can freely bend in either of two directions of the upward and downward directions, or in either of two directions of the left and right directions, or any of four directions of the upward, downward, left, and right directions. Here, a shaft body of the bending operation lever is extended from the inside of the operation unit to the outside of the operation unit through a hole located in an exterior casing of this operation unit. At the extension end that is an end part of the shaft body, an operation element is located. The operation element is gripped by an operator when the shaft body is tilted by the operator. Furthermore, a seal unit is externally mounted on the shaft body. The seal unit prevents entry of liquid, dust and dirt, and the likes into the operation unit by covering a hole of the operation unit. The seal unit has an elastic member formed into a sheet shape and into a shape of a circle substantially concentric with the shaft body. The elastic member is made of rubber or the like.

The inner circumferential edge of the elastic member is attached to the outer circumference of the shaft body. The outer circumferential edge of the elastic member is locked and attached to a fixing hole or the like made in the exterior casing of the operation unit for example. Furthermore, in Japanese Patent 2005-279119A, a configuration is disclosed in which an elastic member is formed into an accordion shape and into an umbrella shape. The amount of tilting force of a shaft body of a bending operation lever may become small when the shaft body is tilted. Moreover, in Japanese Patent 2005-279119A, a configuration is disclosed in which a gap is made between a region opposed to the outer circumference of the shaft body in the accordion-shaped elastic member and the outer circumference of the shaft body. Hereinafter, the region is referred to as the "opposed region". From the above, a configuration in which space is ensured for extension of the elastic member when the shaft body is tilted being disclosed in Japanese Patent 2005-279119A. However, one of the shortcoming of the prior art is that the opposed region sticks to the outer circumference of the shaft body in association with the inflation and the sticking region becomes difficult to clean and sterilize.

Therefore, there is a need for an endoscope having a bending operation mechanism to rectify, among others, the aforementioned problems.

BRIEF SUMMARY OF EMBODIMENTS

One aspect of the technology disclosed herein is directed to a bending operation mechanism of an endoscope that includes a bending operation lever and a seal unit. The bending operation lever is tilted to bend a bending part disposed in an insertion unit of the endoscope. The seal unit is externally mounted on a shaft body of the bending operation lever. The seal unit includes a tubular member having stiffness into which the shaft body is fitted. The seal unit has a sheet-shaped elastic member molded integrally with the tubular member. The elastic member has a stationary part and an extending part. The stationary part is attached to an outer circumference of the tubular member in a circumferential manner along a longitudinal axis direction of the tubular member. The extending part extends from an outer circumference of the stationary part to the outside of the stationary part in a radial direction into a shape of a circle substantially concentric with the stationary part. In the extending part, there is a region extends from the outer circumference of the stationary part with a predetermined angle.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Incidentally, generally a water leakage test of an endoscope is carried out before cleaning-sterilization treatment of the endoscope is carried out.

In the water leakage test, a gas is supplied to the inside of the endoscope. In association with the supply of the gas, the gas is also passed to the seal unit and becomes inflates through the hole of the exterior casing of the operation unit. At this time, if a gap is formed between the "opposed region" of the elastic member and the outer circumference of the shaft body as in the configuration disclosed in Japanese Patent 2005-279119A, a deformation footprint is formed in the opposed region in association with the repetition of tilt operation of the shaft body. There is a problem that, due to this, the deformation shape at the time of gas supply in the water leakage test is unstable in the opposed region. Thus, there is a problem that, depending on the deformation footprint, the opposed region sticks to the outer circumference of the shaft body in association with the inflation. Also, the opposed region remains sticking even after stop of the gas supply, i.e. even after deflation of the elastic member. Therefore, the sticking region becomes difficult to clean and sterilize.

The technology disclosed herein is made in view of the above-described problems and intends to provide a bending operation mechanism of an endoscope having a configuration that can equalize the shapes of a seal unit before and after inflation and deflation.

An embodiment of the present disclosure will be described below with reference to the drawings. It should be noted that the drawings are schematic and (i) the relationship between the thickness and width of each member, (ii) the ratio of the thicknesses of the respective members, and so forth are different from actual ones. It is obvious that parts different in the relationship and ratio of the respective dimensions also between the drawings are included.

Figure 1:
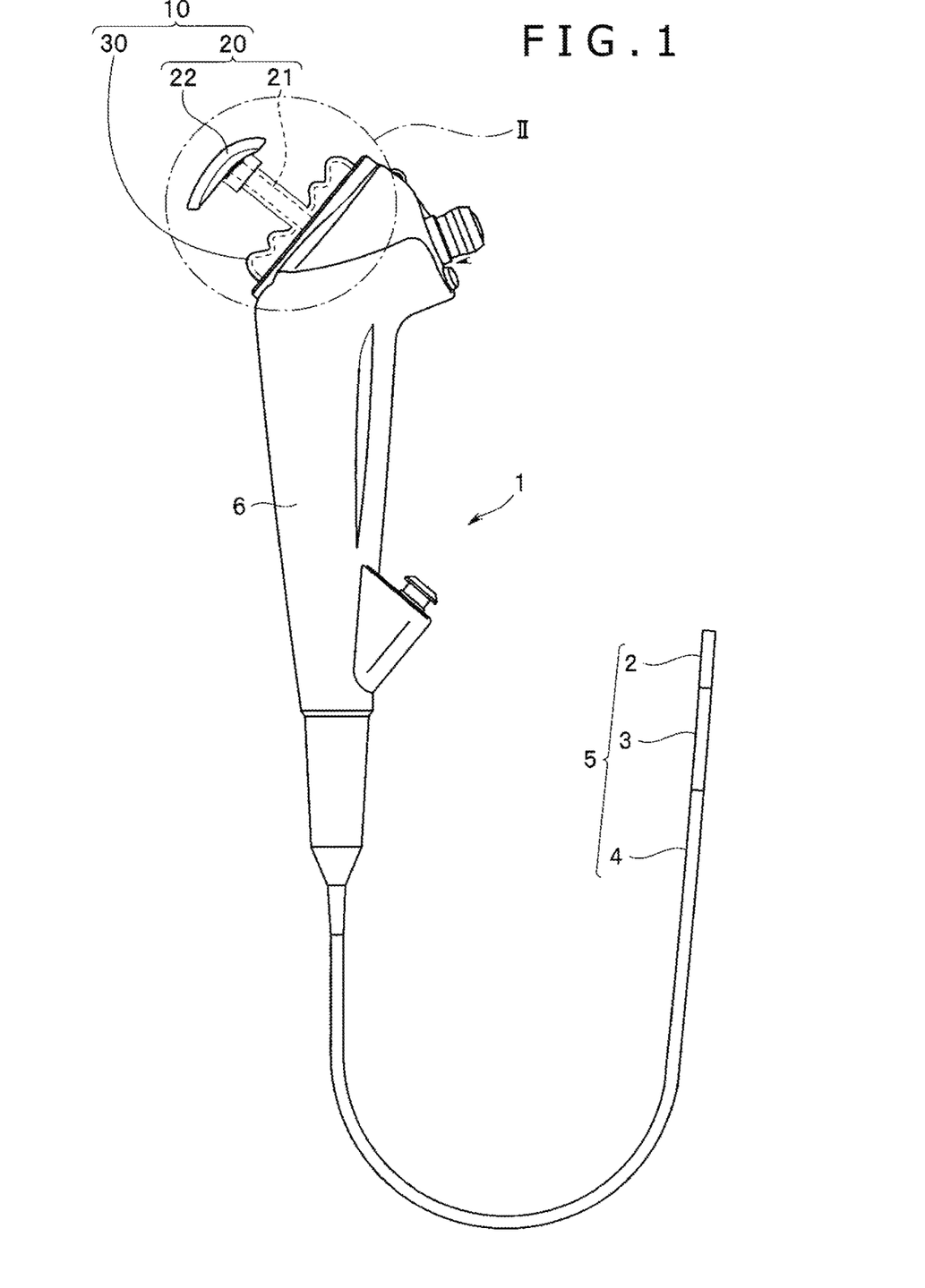
FIG. 1 is a perspective view of an endoscope including a bending operation mechanism according to the technology described herein.

FIG. 1 is a perspective view of an endoscope including a bending operation mechanism of an endoscope according to the present embodiment. As depicted in FIG. 1, an endoscope 1 includes an insertion unit 5 and an operation unit 6. The insertion unit 5 is inserted into a subject such as human body and the like. The operation unit 6 is disposed consecutively at the proximal side of this insertion unit 5. A universal cord, which is not diagrammatically represented, is extended from the operation unit 6. The endoscope 1 is electrically connected to external devices such as a control device and an illuminating device through various connectors. The connectors are disposed at the extension end of the universal cord are not diagrammatically represented. The insertion unit 5 is configured to include a distal part or distal end 2, a bending part 3, and a flexible tube part 4 in that order from the distal part or distal end. The insertion unit 5 is formed into a thin, long tubular shape.

The bending part 3 is bent in the multiple directions, for example, four directions namely, upward, downward, left, and right directions, by manipulating a bending operation lever 20 described hereinafter. Due to this, the bending part 3 allows change in the observation direction of an observation optical system. The optical system is disposed in the distal part 2 and is not diagrammatically shown and is disposed. The bending part 3 improves the insertability of the distal part 2 into a subject such a human body and the like. Moreover, the flexible tube part 4 is disposed consecutively in the proximal side of the bending part 3.

The operation unit 6 includes a bending operation mechanism 10 of the endoscope 1. The bending operation mechanism 10 includes a bending operation lever 20 and a seal unit 30. The bending operation lever 20 is tilted to bend the bending part 3. The bending operation lever 20 includes a shaft body 21 and an operation element 22. The operation element 22 is disposed at one end part of the shaft body 21. The other end part of the shaft body 21 is connected to a device, which is not diagrammatically represented. The device is disposed in the operation unit 6 and bends the bending part 3 in association with the tilt of the bending operation lever 20. The shaft body 21 is extended to the outside of the operation unit 6 through a hole 6v formed in an exterior casing 6k as seen best in FIG. 2 and is described hereinafter for the operation unit 6. The operation element 22 is disposed at the extension end of the shaft body 21.

Figure 2:
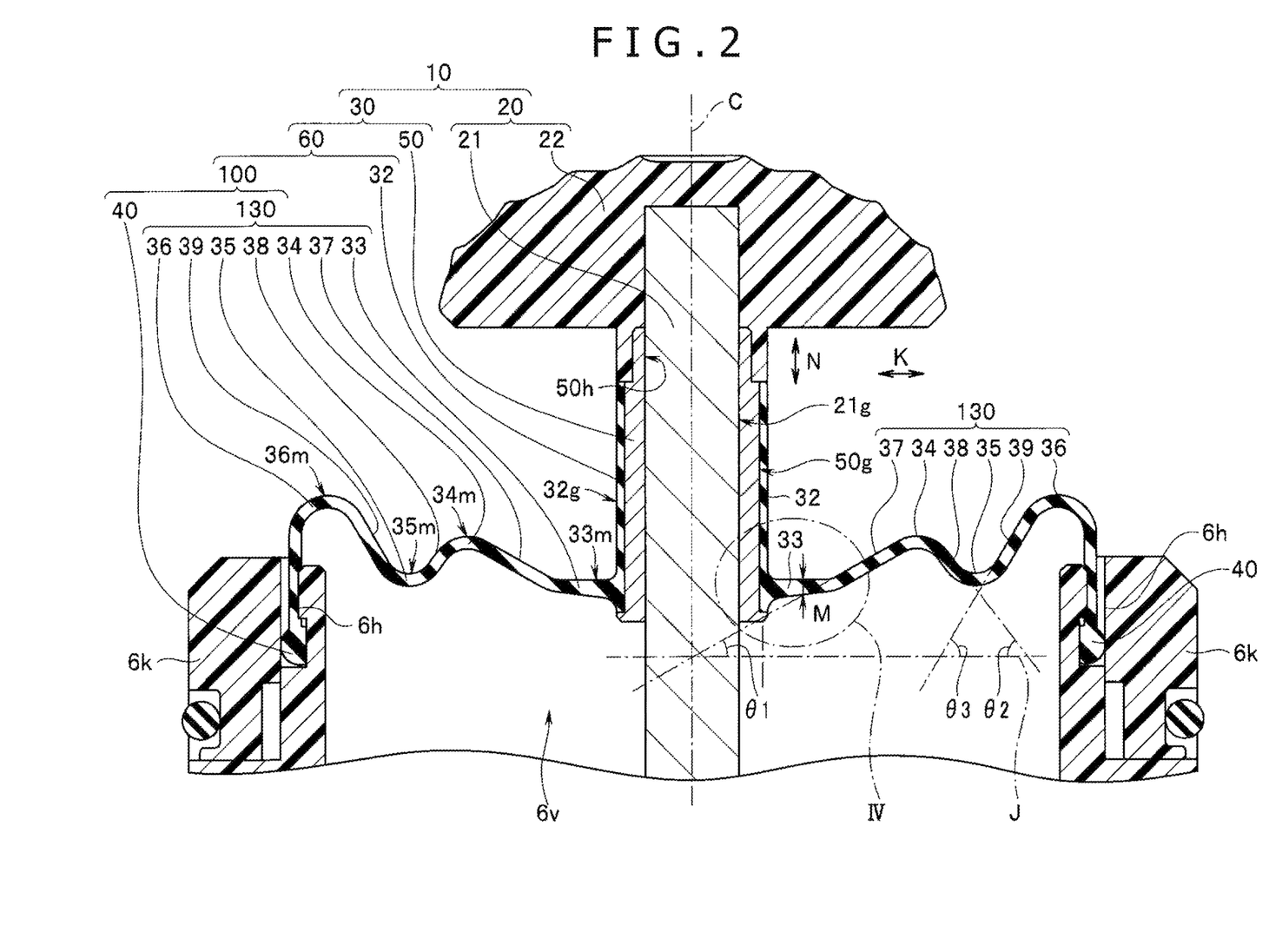
FIG. 2 is a sectional view depicting the bending operation mechanism of the endoscope surrounded by line II in FIG. 1 with part of an exterior casing of an operation unit.
Figure 3:
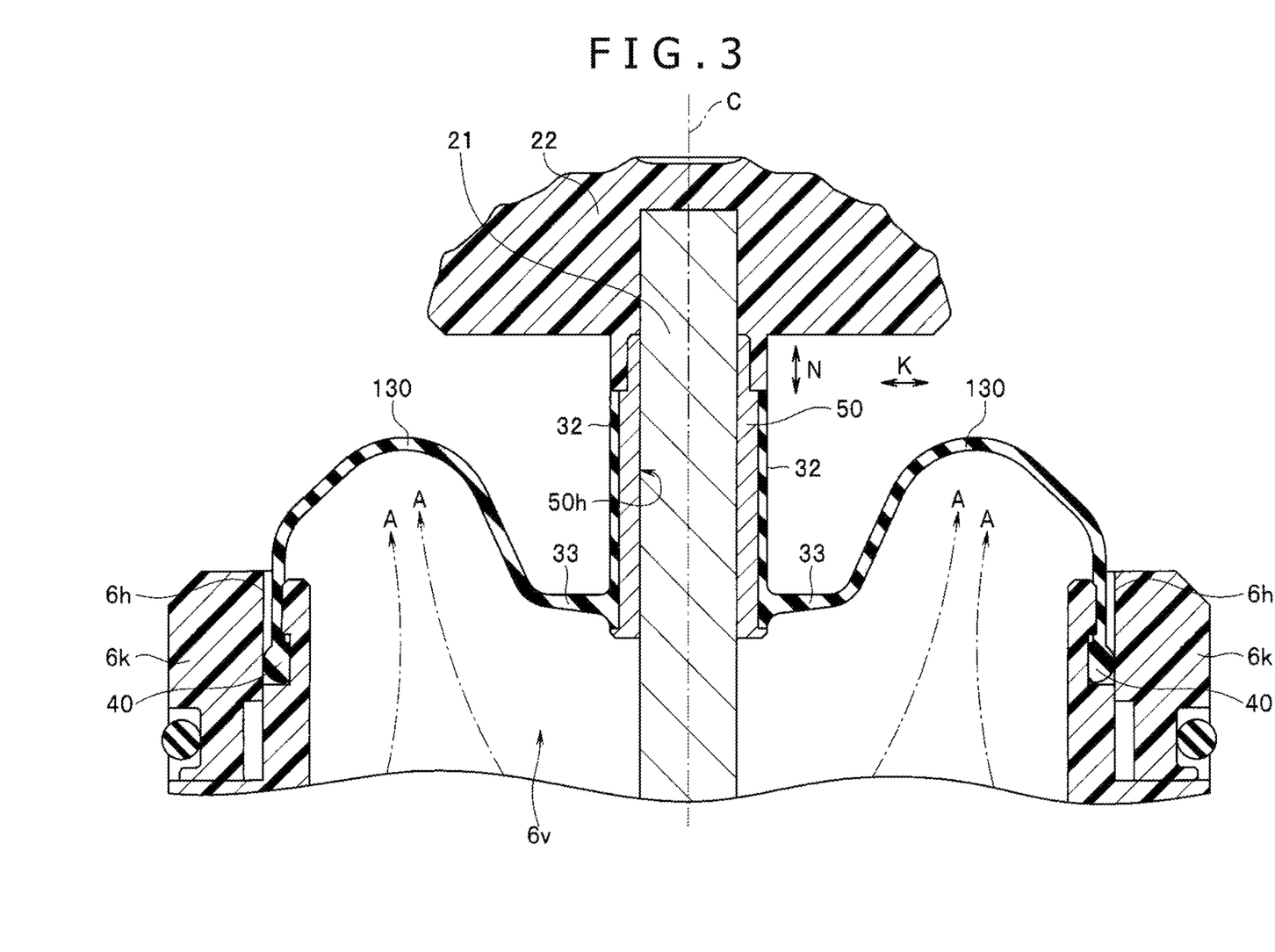
FIG. 3 is a sectional view depicting the state in which an elastic member of a seal unit in FIG. 2 has inflated due to supply of a gas.
Figure 4:
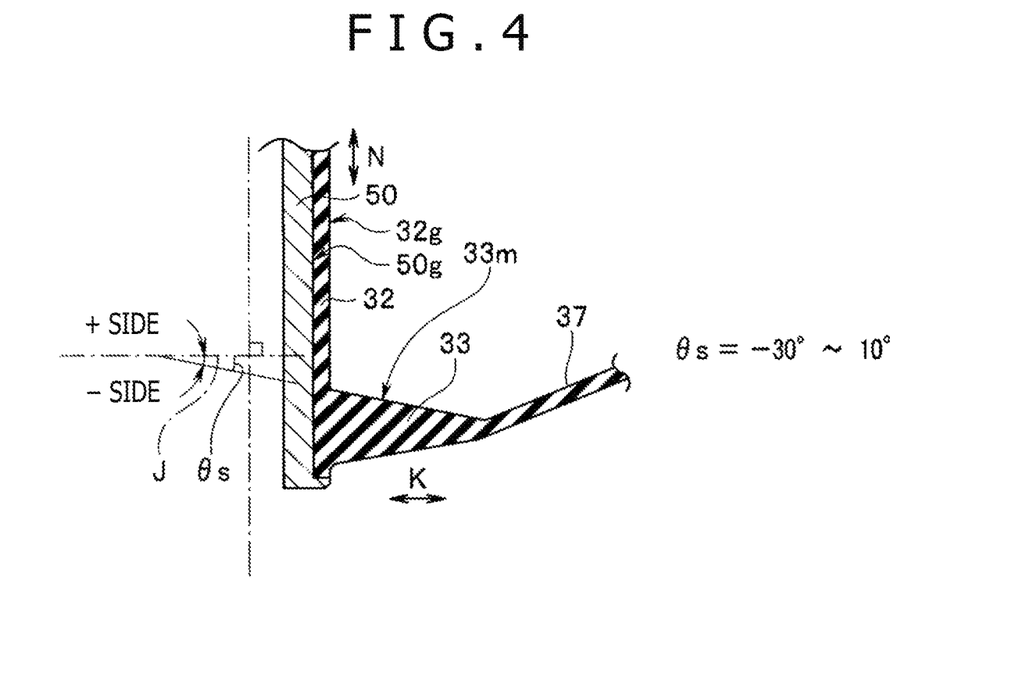
FIG. 4 is an enlarged sectional view of a region of the seal unit surrounded by line IV in FIG. 2.
Figure 5:
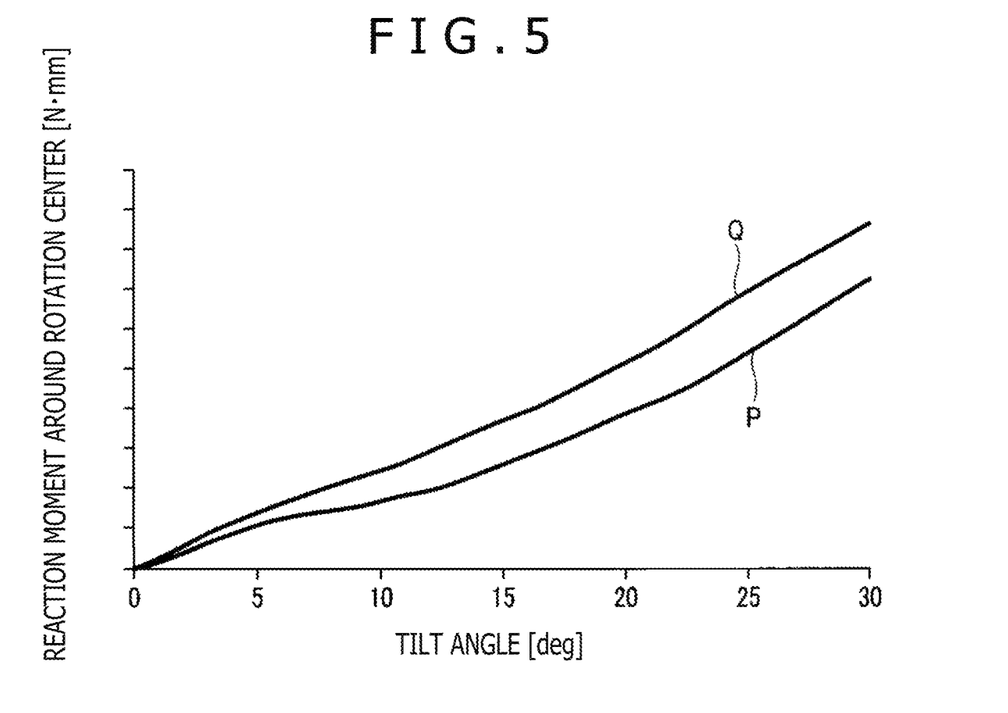
FIG. 5 is a graph depicting the reaction moment with respect to the tilt angle when a bending operation lever in FIG. 2 is tilted with comparison with a conventional technique.

Next, the configuration of the seal unit 30 will be described by using FIG. 2 to FIG. 5. FIG. 2 is a sectional view depicting the bending operation mechanism of the endoscope surrounded by line II in FIG. 1 with part of the exterior casing of the operation unit. FIG. 3 is a sectional view depicting the state in which an elastic member of the seal unit in FIG. 2 has inflated due to supply of a gas. FIG. 4 is an enlarged sectional view of a region of the seal unit surrounded by line IV in FIG. 2. FIG. 5 is a chart depicting the reaction moment with respect to the tilt angle when the bending operation lever in FIG. 2 is tilted with comparison with a conventional technique.

As depicted in FIG. 2, the seal unit 30 is externally mounted on the shaft body 21 of the bending operation lever 20. Furthermore, a locked part 40 is disposed at the outer circumferential edge and described hereinafter. The locked part 40 is locked and attached to the exterior casing 6k so that the seal unit 30 closes the hole 6v. As a result, the seal unit 30 prevents entry of liquid, dust and dirt, and so forth into the operation unit 6 through the hole 6v. Moreover, the seal unit 30 includes a tubular member 50 and a sheet-shaped elastic member 60. The open-ended tubular member 50 has a hole 50h and receives the shaft body 21 along a longitudinal axis direction N. The tubular member 50 is constituted of a material having stiffness, such as stainless steel. The elastic member 60 is formed integrally with the tubular member 50 by insert molding or the like. Furthermore, the elastic member 60 is formed into a sheet shape with a thickness of, for example, 1 mm from for example, silicone rubber having hardness of 30 to 70 degrees in the Shore D scale. The material forming the elastic member 60 is not limited to silicone rubber. Furthermore, the thickness of the elastic member 60 is not limited to 1 mm.

The elastic member 60 includes a stationary part 32 and an extending part 100. The stationary part 32 is attached to an outer circumference 50g of the tubular member 50 in a circumferential manner along the longitudinal axis direction N of the tubular member 50. That is, the elastic member 60 is formed integrally with the tubular member 50 at the stationary part 32. The extending part 100 extends from an outer circumference 32g of the stationary part 32 to the outside of the stationary part 32 in a radial direction K into a shape of a circle substantially concentric with the stationary part 32 and in a circumferential manner. In addition, a region 33 extends from the outer circumference 32g and extends with a predetermined angle θs as seen best in FIG. 4.

As depicted in FIG. 4, an axis J is orthogonal to the outer circumference 32g and is parallel to the radial direction K. A surface 33m is on the side of the operation element 22 in the longitudinal axis direction N in the region 33. The predetermined angle θs is the angle between an axis J and a surface 33m and is set in a range of −30° to 10°. The angle θs is set based on the axis J and the extension line of the surface 33m. The negative sign "−" in the angle θs is corresponding to the case in which the angle θs is located on the opposite side to the operation element 22 in the longitudinal axis direction N relative to the axis J as depicted in FIG. 4. Furthermore, the positive sign "+" is corresponding to the case in which the angle θs is located on the side of the operation element 22 in the longitudinal axis direction N relative to the axis J. The extending part 100 includes a first recessed part 33, a first projected part 34, a second recessed part 35, a second projected part 36, a first inclined surface 37, a second inclined surface 38, a third inclined surface 39, and the locked part 40. The first recessed part 33 forms the above-described region 33 that extends from the outer circumference 32g of the stationary part 32. In addition, a first recessed surface 33m is formed on the side of the operation element 22 in the longitudinal axis direction N.

Wall thickness M of the first recessed part 33 is formed to be 1 to 1.5 mm, for example, in such a manner as to become larger as the position gets closer to the stationary part 32. The numerical value of the wall thickness M is not limited thereto. The first projected part 34 is located outside the first recessed part 33 in the radial direction K. A first projected surface 34m is formed on the side of the operation element 22 in the longitudinal axis direction N. The second recessed part 35 is located outside the first projected part 34 in the radial direction K. A second recessed surface 35m is formed on the side of the operation element 22 in the longitudinal axis direction N. The second recessed surface 35m is located on the side of the operation element 22 relative to the first recessed surface 33m. The second projected part 36 is located outside the second recessed part 35 in the radial direction K. A second projected surface 36m is formed on the side of the operation element 22 in the longitudinal axis direction N. The second projected surface 36m is located on the side of the operation element 22 relative to the first projected surface 34m. The first inclined surface 37 connects the first recessed part 33 and the first projected part 34 in the radial direction K. An inclination angle θ1 with respect to the axis J is set to 10° to 70°, and preferably to 60°. The second inclined surface 38 connects the first projected part 34 and the second recessed part 35 in the radial direction K. An inclination angle θ2 with respect to the axis J is set to 10° to 70°, and preferably to 60°.

The third inclined surface 39 connects the second recessed part 35 and the second projected part 36 in the radial direction K. An inclination angle θ3 with respect to the axis J is set to 10° to 70°, and preferably to 60°. The first recessed part 33, the first inclined surface 37, the first projected part 34, the second inclined surface 38, the second recessed part 35, the third inclined surface 39, and the second projected part 36 form a region 130. The region 130 inflates in the elastic member 60 as depicted in FIG. 2 and FIG. 3 when (i) a gas "A" is introduced to the inside of the operation unit 6 in a water leakage test of the endoscope 1 and (ii) the gas A is introduced also to the inside of the elastic member 60 via the hole 6v and (iii) the internal pressure of the elastic member 60 becomes higher, for example, becomes a positive pressure. Furthermore, as described hereinbefore, in the present embodiment, the first recessed part 33, the first inclined surface 37, the first projected part 34, the second inclined surface 38, the second recessed part 35, the third inclined surface 39, and the second projected part 36 all of which are formed in the accordion shape, and θ1, θ2, and θ3 are set to 10° to 70°. It has turned out that, due to this, after inflation and deflation of the region 130, the region 130 returns to the shape before the inflation and deflation due to the resilience (elastic force) of this region 130. In other words, the first inclined surface 37 to the second projected part 36 return to the shape before the inflation in a matching manner.

The locked part 40 is formed at the outer circumferential edge. The outer circumferential edge is the extension end of the extending part 100. The locked part 40 is fitted and attached into a locking groove 6h formed in the exterior casing 6k of the operation unit 6. The other configuration of the bending operation mechanism 10 is the same as conventional ones. As described hereinbefore, in the present embodiment, it is depicted that the seal unit 30 has the tubular member 50 having stiffness into which the shaft body 21 is fitted. Furthermore, it is depicted that the elastic member 60 is formed integrally with the tubular member 50 and the elastic member 60 has the stationary part 32. The stationary part 32 is attached to the outer circumference 50g of the tubular member 50 in a circumferential manner along the longitudinal axis direction N. According to this, even when tilt operation of the bending operation lever 20 is carried out multiple times, it is difficult for a deformation footprint to be made in the stationary part 32 due to the tubular member 50 having stiffness.

As a result, even when the pressure in the elastic member 60 becomes a positive pressure, the elastic member 60 does not stick directly to the shaft body 21 due to the tubular member 50. In addition, because a deformation footprint is absent in the stationary part 32, the stationary state of the stationary part 32 to the outer circumference 50g of the tubular member 50 can be kept. Furthermore, the stationary part 32 is attached to the tubular member 50 along the longitudinal axis direction N. Therefore, it is possible to prevent formation of a recessed part in association with a deformation footprint of the elastic member 60 in this elastic member 60 after inflation and deflation of the elastic member 60. Thus, the performance of cleaning and sterilization for the elastic member 60 can be improved.

Moreover, in the present embodiment, it is depicted that the first recessed part 33 in the extending part 100 of the elastic member 60 extends from the outer circumference 32g of the stationary part 32 with the above-described angle θs set to −30° to 10°. According to this, the first recessed surface 33m of the first recessed part 33 is not opposed to the outer circumference 32g of the stationary part 32. Therefore, even when the pressure in the elastic member 60 becomes a positive pressure and the region 130 inflates, it is difficult for the first recessed part 33 to stick to the outer circumference 32g of the stationary part 32. As described above, the wall thickness M of the first recessed part 33 becomes larger as the position gets closer to the outer circumference 32g. Therefore, the first recessed part 33 sticks to the outer circumference 32g due to inflation less readily. This avoids the lowering of the performance of cleaning and sterilization due to (i) sticking of the first recessed part 33 to the outer circumference 32g and (ii) keeping of the sticking state even after deflation of the region 130. Furthermore, it is depicted that the extending part 100 of the elastic member 60 is formed into the above-described accordion shape from the first recessed part 33 to the second projected part 36.

According to this, although the stationary part 32 is attached to the outer circumference 50g of the tubular member 50 along the longitudinal axis direction N, room or space for extension is ensured by the parts from the first recessed part 33 to the second projected part 36 when the shaft body 21 is tilted. For this reason, as depicted in FIG. 5, a reaction moment (N·mm) "P" around a rotation center C with respect to the tilt angle of the shaft body 21 can be made lower than a moment "Q" when recesses and projections do not exist in the extending part 100. That is, although the attached part 32 is attached to the outer circumference 50g of the tubular member 50 along the longitudinal axis direction "N", the amount of tilting force of the bending operation lever 20 can be made small. Furthermore, θ1 to θ3 are set to 10° to 70°. Due to this, after inflation and deflation of the region 130, the region 130 can be surely returned to the shape before the inflation based on the resilience (elastic force) of this region 130.

From the above, the bending operation mechanism 10 of an endoscope having a configuration that can balance the shapes of the seal unit 30 before and after inflation and deflation can be provided.

In sum, one aspect of the disclosed technology is directed to a bending operation mechanism of an endoscope comprises a bending operation lever being tilted to bend a bending part disposed at an insertion unit of the endoscope. A seal unit is externally mounted on a shaft body of the bending operation lever and includes a tubular member having stiffness into which the shaft body is fitted therethrough. A sheet-shaped elastic member is molded integrally with the tubular member. The sheet-shaped elastic member includes a stationary part being attached to an outer circumference of the tubular member in a circumferential manner along a longitudinal axis direction of the tubular member. An extending part that extends from an outer circumference of the stationary part to outside of the stationary part in a radial direction into a shape of a circle substantially concentric with the stationary part. A region that extends from the outer circumference of the stationary part extends with a predetermined angle.

The predetermined angle is an angle between an axis that is orthogonal to the outer circumference of the stationary part and is parallel to the radial direction and a surface on a side of an operation element disposed at an end part of the shaft body of the bending operation lever in the region extending from the outer circumference of the stationary part and wherein the angle is set to be from −30° to +10°. The extending part includes a first recessed part that forms the region extending from the outer circumference of the stationary part. A first recessed surface is formed on a side of an operation element disposed at an end part of the shaft body of the bending operation lever. A first projected part is located outside the first recessed part in the radial direction where a first projected surface is formed on the side of the operation element. A second recessed part is located outside the first projected part in the radial direction and a second recessed surface is located on the side of the operation element relative to the first recessed surface that is formed on the side of the operation element. A second projected part is located outside the second recessed part in the radial direction and a second projected surface is located on the side of the operation element relative to the first projected surface that is formed on the side of the operation element. A locked part located outside the second projected part in the radial direction disposed at an outer circumferential edge part as an extension end of the extending part and is locked to an operation unit of the endoscope.

The first recessed part includes a wall thickness becomes larger as a position gets closer to the stationary part. The first recessed part and the first projected part are connected by a first inclined surface and an inclination angle being set from 10° to 70° of the first inclined surface with respect to an axis that is orthogonal to the outer circumference of the stationary part and is parallel to the radial direction. The first projected part and the second recessed part are connected by a second inclined surface and an inclination angle being set from 10° to 70° of the second inclined surface with respect to an axis that is orthogonal to the outer circumference of the stationary part and is parallel to the radial direction. The second recessed part and the second projected part are connected by a third inclined surface and an inclination angle being set from 10° to 70° of the third inclined surface with respect to an axis that is orthogonal to the outer circumference of the stationary part and is parallel to the radial direction is set to 10° to 70°.

Another aspect of the disclosed technology is directed to a bending operation mechanism of an endoscope that comprises a bending operation lever including a shaft body and an operation element. The operation element is disposed at an end part of the shaft body. The bending operation lever is configured to bend a bending part disposed at an insertion unit of the endoscope. A seal unit is externally mounted on the shaft body and including a tubular member and a sheet-shaped elastic member. The shaft body is fitted in the tubular member. The sheet-shaped elastic member is molded integrally with the tubular member. The sheet-shaped elastic member includes a stationary part attached to an outer circumference of the tubular member along a longitudinal axis direction of the tubular member. An extending part extends from an outer circumference of the stationary part to outside of the stationary part in a radial direction. The extending part is a shape of a circle substantially concentric with the stationary part and the extending part includes a region that extends from the outer circumference of the stationary part with a predetermined angle.

The predetermined angle is an angle between an axis and a surface. The axis is orthogonal to the outer circumference of the stationary part and is parallel to the radial direction. The surface is on a side of the operation element in the region and the angle is set to −30° to +10°. The extending part includes a first recessed part forming the region and including a first recessed surface. The first recessed surface is formed on a side of the operation element. A first projected part is located outside the first recessed part in the radial direction and including a first projected surface. The first projected surface is formed on the side of the operation element. A second recessed part is located outside the first projected part in the radial direction and including a second recessed surface. The second recessed surface is located on the side of the operation element relative to the first recessed surface and is formed on the side of the operation element. A second projected part is located outside the second recessed part in the radial direction and including a second projected surface. The second projected surface is located on the side of the operation element relative to the first projected surface and is formed on the side of the operation element. A locked part is located outside the second projected part in the radial direction that formed as an extension end of the extending part and locked to an operation unit of the endoscope.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A bending operation mechanism of an endoscope, comprising:
    a bending operation lever being tilted to bend a bending part disposed at an insertion unit of the endoscope;
    a seal unit being externally mounted on a shaft body of the bending operation lever and includes a tubular member having stiffness into which the shaft body being fitted therethrough,
    a sheet-shaped elastic member being molded integrally with the tubular member; and
    an operation element disposed at a proximal end of the shaft body of the bending operation lever and in contact with the sheet-shaped elastic member, the operation element is configured to be pressed by a finger of an operator, the proximal end of the shaft body being on a proximal end of the endoscope, the sheet-shaped elastic member including:
        a stationary part being attached to an outer circumference of the tubular member in a circumferential manner along a longitudinal axis direction of the tubular member; and
        an extending part that extends from an outer circumference of the stationary part to outside of the stationary part in a radial direction into a shape of a circle substantially concentric with the stationary part and wherein a region that extends from the outer circumference of the stationary part extends with a predetermined angle, the extending part including:
            a first recessed part that extends from the outer circumference of the stationary part;
            a first projected part spaced from the first recessed part in the radial direction;
            a second recessed part spaced from the first projected part in the radial direction and provided closer to an outer surface of the proximal end than the first recessed part in an axial direction of the shaft body;
            a second projected part spaced from the second recessed part in the radial direction;
            a locked part that is attached to an operation unit of the endoscope, the locked part being spaced from the second projected part in the radial direction and disposed at an outer circumferential edge part, the locked part being an extension end of the extending part.

2. The bending operation mechanism of the endoscope of claim 1, wherein the predetermined angle is an angle between an axis that is orthogonal to the outer circumference of the stationary part and is parallel to the radial direction and a surface on a side of the operation element disposed at an end part of the shaft body of the bending operation lever in the region extending from the outer circumference of the stationary part and wherein the angle is set to be from −30° to +10°.

3. The bending operation mechanism of the endoscope of claim 1, wherein the second projected part is provided closer to the outer surface of the proximal end than the first projected part in the axial direction of the shaft body.

4. The bending operation mechanism of the endoscope of claim 3, wherein the first recessed part includes a wall thickness that becomes larger as a position gets closer to the stationary part.

5. The bending operation mechanism of the endoscope of claim 3, wherein the first recessed part and the first projected part are connected by a first inclined surface and an inclination angle being set from 10° to 70° of the first inclined surface with respect to an axis that is orthogonal to the outer circumference of the stationary part and is parallel to the radial direction.

6. The bending operation mechanism of the endoscope of claim 3, wherein the first projected part and the second recessed part are connected by a second inclined surface and an inclination angle being set from 10° to 70° of the second inclined surface with respect to an axis that is orthogonal to the outer circumference of the stationary part and is parallel to the radial direction.

7. The bending operation mechanism of the endoscope of claim 3, wherein the second recessed part and the second projected part are connected by a third inclined surface and an inclination angle being set from 10° to 70° of the third inclined surface with respect to an axis that is orthogonal to the outer circumference of the stationary part and is parallel to the radial direction is set to 10° to 70°.

8. The bending operation mechanism of the endoscope of claim 1, wherein the stationary part terminates in direct contact with a distal-most surface on the operation element.

9. The bending operation mechanism of the endoscope of claim 1, wherein the second projected part is provided closer to the proximal end of the shaft body than the first projected part in an axial direction of the shaft body.

10. A bending operation mechanism of an endoscope, comprising:
   a bending operation lever including a shaft body and an operation element, the operation element being disposed at a proximal end of the shaft body and being configured to be pressed by a finger of an operator, the bending operation lever being configured to bend a bending part disposed at an insertion unit of the endoscope;
   a seal unit being externally mounted on the shaft body and including a tubular member and a sheet-shaped elastic member, the operation element being in contact with the sheet-shaped elastic member, the shaft body being fitted in the tubular member, the sheet-shaped elastic member being molded integrally with the tubular member; and
   the operation element disposed at an end part of the shaft body of the bending operation lever, the end part of the shaft body being on a proximal end of the endoscope, the sheet-shaped elastic member including:
      a stationary part attached to an outer circumference of the tubular member along a longitudinal axis direction of the tubular member, and
      an extending part extending from an outer circumference of the stationary part to outside of the stationary part in a radial direction, the extending part being a shape of a circle substantially concentric with the stationary part, and the extending part including a region that extends from the outer circumference of the stationary part with a predetermined angle, the extending part including:
         a first recessed part that extends from the outer circumference of the stationary part;
         a first projected part spaced from the first recessed part in the radial direction;
         a second recessed part spaced from the first projected part in the radial direction and provided closer to an outer surface of the end part than the first recessed part in an axial direction of the shaft body;
         a second projected part spaced from the second recessed part in the radial direction; and
         a locked part that is attached to an operation unit of the endoscope, the locked part being spaced from the second projected part in the radial direction and disposed at an outer circumferential edge part, the locked part being an extension end of the extending part.

11. The bending operation mechanism of an endoscope of claim 10, wherein the predetermined angle is an angle between an axis and a surface, the axis being orthogonal to the outer circumference of the stationary part and being parallel to the radial direction, the surface being on a side of the operation element in the region, and the angle is set to −30° to +10°.

12. The bending operation mechanism of an endoscope of claim 10, wherein:
   the second projected part is provided closer to the outer surface of the end part than the first projected part in the axial direction of the shaft body.

13. The bending operation mechanism of an endoscope of claim 10, wherein wall thickness of the first recessed part becomes larger as a position gets closer to the stationary part.

* * * * *